(12) United States Patent
Breen et al.

(10) Patent No.: US 8,127,621 B2
(45) Date of Patent: Mar. 6, 2012

(54) LOCKING MECHANISM WITH ACOUSTIC BARRIER FOR MOUNTING A SENSOR ON A PIPE

(75) Inventors: Ivar Breen, Stavanger (NO); Morten Ivar Andersen, Rådal (NO)

(73) Assignee: Roxar Flow Measurement AS, Bergen (NO)

( * ) Notice: Subject to any disclaimer, the term of this patent is extended or adjusted under 35 U.S.C. 154(b) by 311 days.

(21) Appl. No.: 12/520,601

(22) PCT Filed: Dec. 11, 2007

(86) PCT No.: PCT/NO2007/000436
§ 371 (c)(1),
(2), (4) Date: Nov. 16, 2009

(87) PCT Pub. No.: WO2008/079014
PCT Pub. Date: Jul. 3, 2008

(65) Prior Publication Data
US 2010/0077864 A1    Apr. 1, 2010

(30) Foreign Application Priority Data
Dec. 22, 2006  (NO) .................................. 20065989

(51) Int. Cl.
*G01N 3/02* (2006.01)
(52) U.S. Cl. ........................................ 73/856; 73/801
(58) Field of Classification Search .................... 73/760, 73/801, 856
See application file for complete search history.

(56) References Cited

U.S. PATENT DOCUMENTS

| | | | |
|---|---|---|---|
| 6,112,599 A | 9/2000 | Maki, Jr. | |
| 6,739,203 B1 * | 5/2004 | Feldman et al. | 73/861.27 |
| 7,058,549 B2 * | 6/2006 | Gysling et al. | 702/189 |
| 7,104,125 B2 * | 9/2006 | Harthorn et al. | 73/152.57 |
| 7,552,631 B2 * | 6/2009 | Harthorn et al. | 73/152.57 |
| 7,878,047 B2 * | 2/2011 | Hemblade | 73/61.75 |
| 2006/0225514 A1 | 10/2006 | Conquergood | |

FOREIGN PATENT DOCUMENTS

| | | |
|---|---|---|
| DE | 1 197 23 488 | 12/1998 |
| DE | 10 2004 052489 | 5/2006 |

OTHER PUBLICATIONS

International Search Report for PCT/NO2007/000436 mailed Jul. 2, 2008.
International Preliminary Report on Patentability for PCT/NO2007/000436 completed Apr. 7, 2009.
Norwegian Search Report for NO 2006 5989 dated Jun. 19, 2007.

* cited by examiner

*Primary Examiner* — Max Noori
(74) *Attorney, Agent, or Firm* — Nixon & Vanderhye PC

(57) ABSTRACT

This invention relates to a device for mounting in a fixed mounted frame (7) on a subsea pipe comprising a locking device comprising a sensor housing (6), a spring (2) surrounding the sensor housing (6), at least one wedge (1) placed in one of the ends of the spring (2), and a edge (5*a*) placed in the other end of the spring (2), where the sensor housing (6) is arranged to be guided into the mounting frame (7), and that a force (13) is applied in the longitudinal axis of the sensor housing (6) so that the spring (2) is compressed and the wedge(s) (1) are spanned radial out towards the mounting frame (7) to center and support the sensor housing (6) in the mounting frame (6), the sensor housing (6) is designed to fit into the mounting frame (7).

11 Claims, 4 Drawing Sheets

LOCKING MECHANISM WITH ACOUSTIC BARRIER FOR MOUNTING A SENSOR ON A PIPE

Figure 1A:
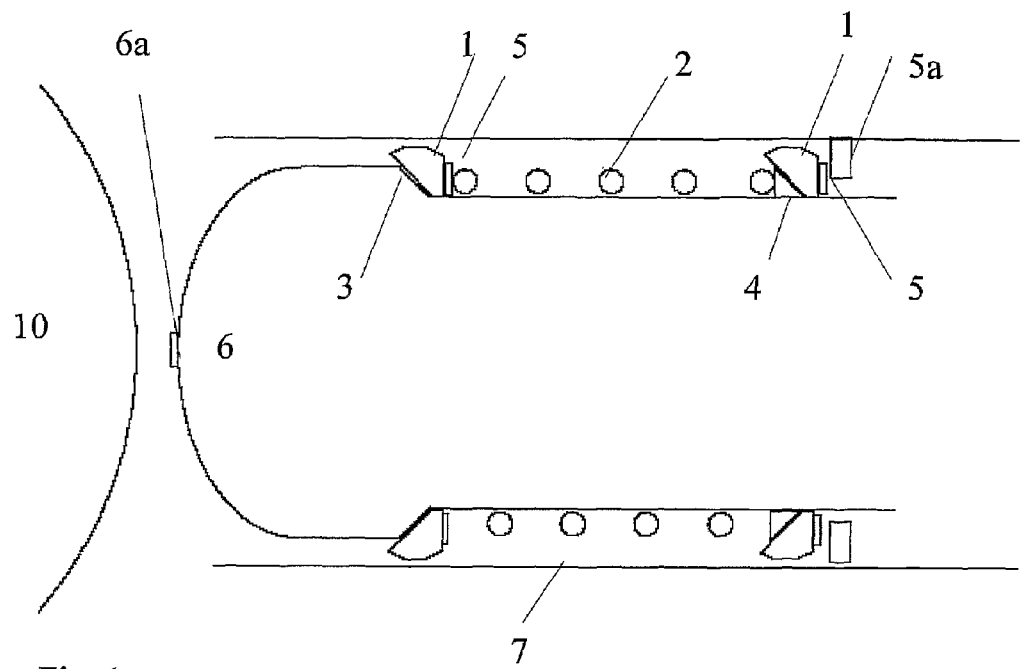

This application is the U.S. national phase of International Application No. PCT/NO2007/000436 filed 11 Dec. 2007 which designated the U.S. and claims priority to Norway Patent Application No. 2006 5989 filed 22 Dec. 2006, the entire contents of each of which are hereby incorporated by reference.

The present invention relates to a general principle and a technical solution for mounting of sensors on the outside of pipes. The invention is especially adapted (but not limited to) acoustic sensors post-mounted on pipe systems on the sea floor by means of remote subsea vehicles, so-called ROV (Remotely Operated Vehicle).

Passive acoustic sensor systems are well established technologies for, among others, detection of sand and passing cleansing spikes in oil, gas and multiphase pipe flow. Sensors "listen" to the relevant fluid guiding pipeline and withdraw information by analysis of intercepted acoustic noise in the ultrasound area. A continuous measurement and monitoring of possible sand production enables optimisation of the production rate for individual wells and gives an operator important input for continuous evaluation of erosion in pipes and vents, and on intrusive process equipment. Reliable sand detection is therefore important both from economic and safety aspects.

A metallic pipe wall is a good conductor for sound. Acoustic sensors can therefore effectively listen to pipe flow from the outside, i.e. with external mounting and physical/acoustic contact with the outer pipe wall. This way, direct exposure towards the process is avoided, the complexity becomes substantially smaller and post-mounting or possibly change of a complete sensor on the sea floor is practical possible.

Mounting mechanisms for this type of sensor comprises briefly normally a funnel formed or cylindrical frame fixed attached to the pipe, where the frame shall provide centring of the sensor and possibility for locking in a suitable position, and a spring mechanism in the unit itself providing a sufficient pressure towards the pipe for good mechanical/acoustic contact. The principle for locking must be simple and robust for safe handling by ROV. Together, this offers special challenges for passive acoustic sensors.

The spring mechanism is normally surrounded by a movable outer cap on the outside of the sensor housing itself, and it is this cap which is normally centred and supported sidewise in the mounting frame, not directly the sensor housing with the sensor head. This is far from ideally, because even a small movement in the sensor with the contact point towards the pipe will affect the acoustic coupling and with that the primary measurement itself. This is a practical and relevant problem with for instance ocean flows pulling the sensor cable and vibrations in the pipe structure from adjacent pumps etc.

Side support of sensor further offers a problem where one wants a fixed anchoring and a largest possible degree of acoustic isolation out towards the mounting frame at the same time. Unwanted noise in the frame will otherwise propagate directly into the sensor house, but sensitivity is wanted apparently concentrated to the contact point towards the pipe where the measurement medium is flowing on the inside. In practice, this involves that direct metallic contact towards the frame should be avoided in the largest possible extent. At the same time, the locking device for spring pressure must normally be of metal with regard to robustness.

From the patent publications US A1 200670225514 and DE A1 197 23 488 it is known devices where sensor housings/ultrasound transducers re centred and supported by means of wedges/protrusions.

The present invention face the challenges outlined above. The technical solution provides good sideways support of the sensor housing itself, by means of particular plastic wedges spanning out towards the mounting frame during spring pressure. The wedges are made of a strong industrial plastic with substantial lower acoustic impedance than the sensor housing and the mounting frame, both being made of metal. This result in a large contrast in acoustic impedance in the fastening point itself, so that the wedges at the same time works as an acoustic barrier towards unwanted acoustic monitoring between sensor and mounting frame. The wedges are further mechanically coupled to a locking device in metal providing spring pressures.

The invention is described in more detail below with reference to the appended FIGS. 1-4 illustrating the invention by means of examples.

Figure 1B:
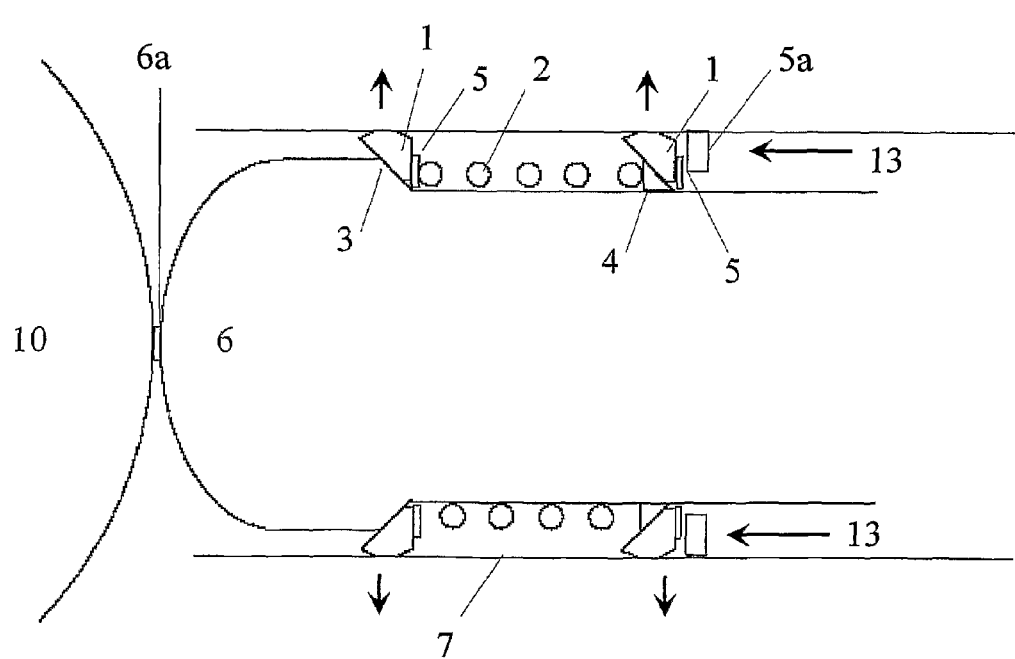

FIGS. 1a and 1b are principle outlines of the inner mechanism for sideways support and centring of the sensor house 6 in the mounting frame 7. FIG. 1a shows the mechanism before the sensor 6a lay towards the pipe 10, and FIG. 1b shows the mechanism with the sensor 6a in locked position on the pipe 10.

Figure 2A:
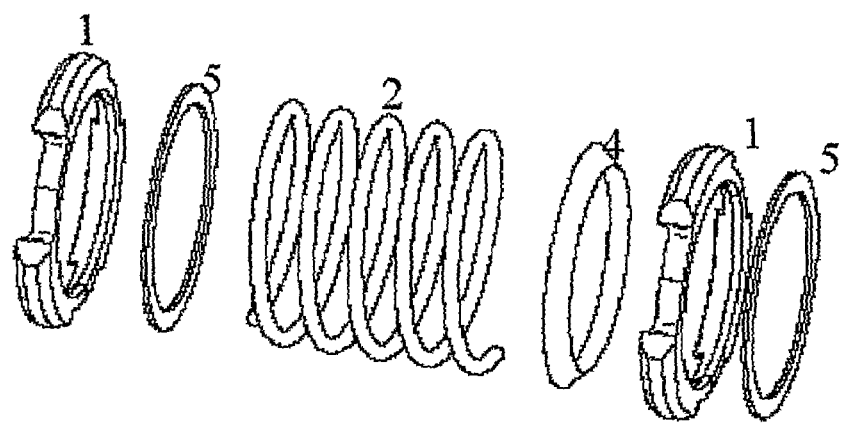
Figure 2B:
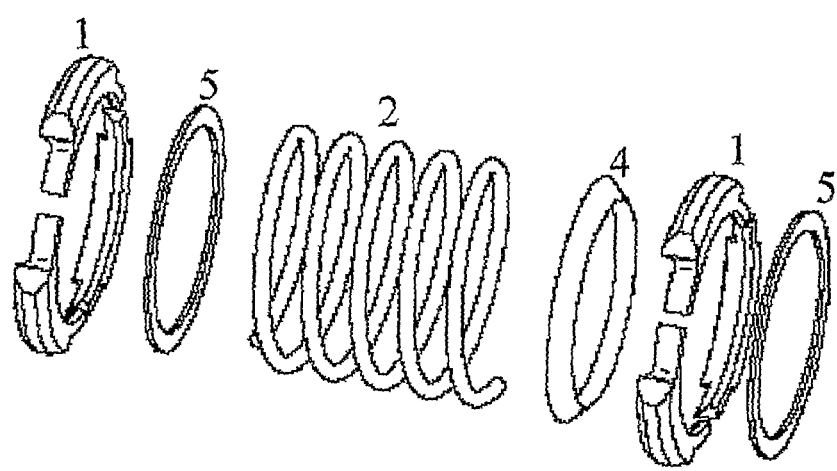

FIG. 2 shows the individual components in the inner mechanism, otherwise illustrated in FIG. 1. FIG. 2a shows the mutual position of the wedges 1 when the spring 2 is not compressed, i.a. before mounting the sensor housing 6 on the pipe. FIG. 2b shows the mutual position of the wedges 1 when the sensor housing 6 is in locked position on the pipes 10.

Figure 3A:
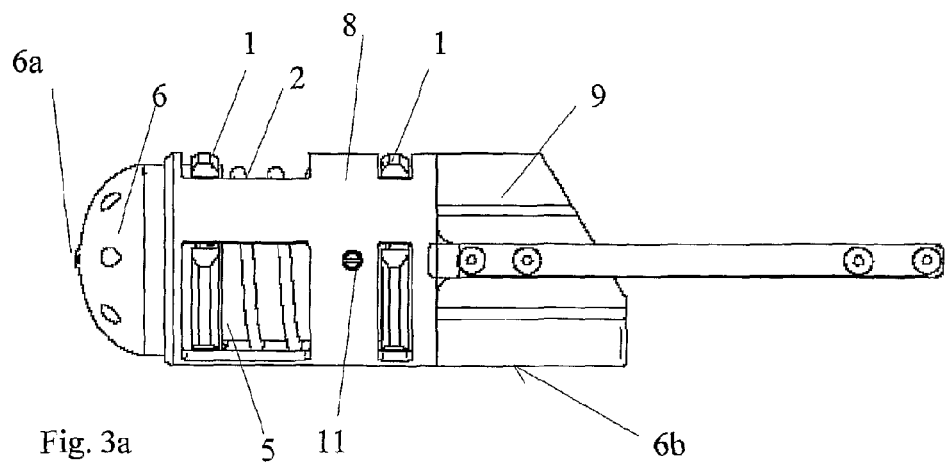
Figure 3B:
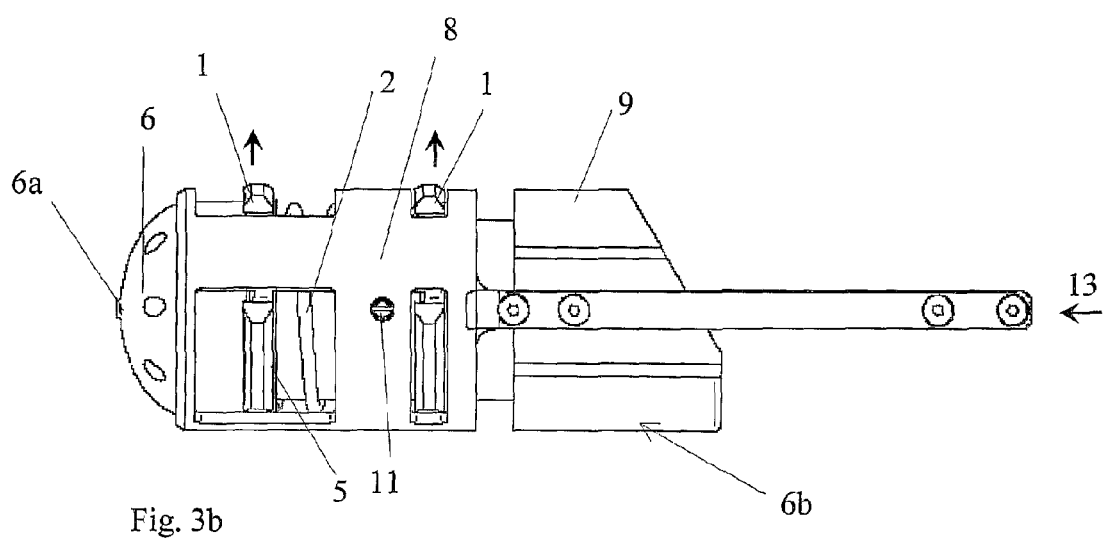

FIG. 3 shows a complete sensor 6b. FIG. 3a shows the complete sensor 6b before mounting on the pipe 10, i.a. with unstrained spring 2. FIG. 3b shows the complete sensor 6b as it appears in locked position on the pipe 10 with compressed spring 2 and spanned wedges 1.

Figure 4:
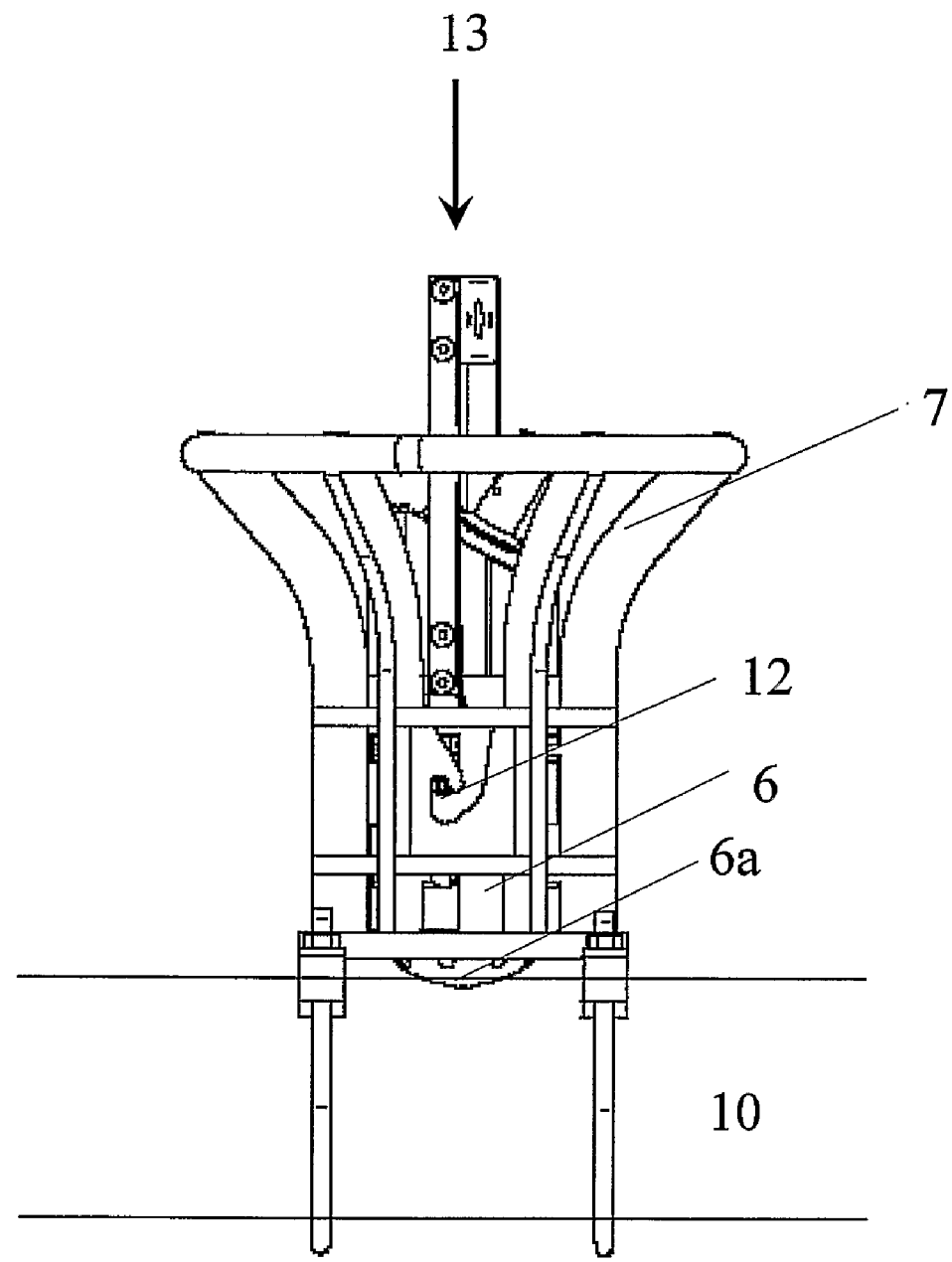

FIG. 4 shows a complete sensor 6b in locked position in the mounting frame 7 on the pipe 10.

With reference to the FIGS. 1-4, the present invention can be described in short form in the following way: The invention has two sets of plastic wedges 1, one on each side of a helical spring 2. The foremost set can slide up towards an inclined surface 3 on the sensor housing 6 itself, while the rear set can slide up towards a conic ring 4 in the back of the spring 2. A flat disk 5 behind the foremost wedge set 1 provides a good and defined sliding surface in the transition towards the helical spring 2. An identical flat disk 5 is preferably arranged behind the rear wedge set 1 to provide equal frictional conditions, so that the rear and foremost wedges 1 move equally. Without pressure on the spring 2, the wedges 1 lay in a circle in towards the smallest diameter on the sensor housing 6, and this can unstrained be led in to a mounting frame 7 on the pipe 10 with clearance to the wedges 1. The inner mechanism is held in place by an outer cap 8, which with an internal edge 5a in the rear end of the cap 7 is guided forward over the sensor housing 6. This happens at first when the sensor 6a lay towards the pipe 10. "Window" in the outer cap 8 opens up for the wedges 1. The cap 8 is on it side held in place by a rear piece 9 comprising an extension of the sensor housing 6. By contact between the sensor 6a and the pipe 10, the spring 2 is compressed gradually as the cap 8 is guided forward, and the wedges 1 slide up the inclined surface 3 and the conic ring 4. The wedges 1 will then be spanned out towards the mounting frame 7, and centres the sensor housing 6 with good side support. Eventually, locking pins 11 on the cap 8 goes into locking tracks 12 in the mounting frame 7, and the sensor housing 6 is held fixed mounted with constant spring pressure towards the pipe 10. Sideway, it is now only the plastic wedges 1 spanning in towards the frame 7.

The primary function of the plastic wedge 1 is centring and supporting, but with substantially lower acoustic impedance than the sensor housing 6 in metal, they work together as an acoustic barrier towards the mounting frame 7. This contributes to prevent absorption of unwanted noise, so that the sensitivity of the sensor housing 6 is concentrated to the contact point towards the pipe 10, where the measurement medium flows on the inside.

The individual figures and the invention in further detail are described below:

In FIG. 1*a*, the sensor housing 6 is shown after it has been guided into the mounting frame 7, but before it is arranged in locking position in towards the pipe 10. The sensor housing 6 is surrounded by a non-compressed helical spring 2. In each end of the spring 2 there are preferably three wedges 1 surrounding the diameter of the sensor housing 6, where the foremost set of wedges 1 are designed to slide up on a inclined surface 3 on the sensor housing 6, and the rear set of wedges 1 is designed to slide up towards a conic ring 4. A flat disk 5 is placed behind the foremost set of wedges 1 to provide a defined slide surface in the transition towards the helical spring 2. An identical flat disk 5 is preferably arranged behind the rear wedge set 1 to provide equal friction conditions, so that the rear and foremost wedges 1 goes equally. An outer cap 8 is preferably mounted around the sensor housing 6, the wedges 1, the conic ring 5 and the flat disks 5 (see FIG. 3). The sensor 6*a* can for instance be a measurement instrument of the same type as shown in the Norwegian patent No 321704.

In FIG. 1*b*, the sensor housing 6 is guided into the mounting frame 7 and put in locked position in towards the pipe 10. The helical spring 2 is compressed as a consequence of a force influence 13, and the foremost and rear wedges 1 have slid up on the inclined surface 3 and the conic ring 4, respectively, and are spanned out towards the mounting frame 7.

FIG. 2*a* shows the components constituting the inner mechanism surrounding the sensor housing 6 when the spring 2 is not compressed, and before the sensor housing 6 is put in locked position in towards the pipe 10. A helical spring 2 has one set of plastic wedges 1 preferably in each end. Each wedge 1 is rounded on the inside so that these tightly surround the outer diameter of the sensor housing 6. A flat disk 5 is placed behind the foremost wedge set 1 as shown in FIG. 1*a* to provide a good and defined slide surface in the transition towards the helical spring 2. In front of the rear wedges 1 lay a conic ring 4 that these wedges 1 shall slide up on at locking the sensor housing 6 in the mounting frame 7 on the pipe 10.

In FIG. 2*b*, the inner mechanism is shown when the spring 2 is compressed (spring compression not shown) and the sensor housing 6 is in locked position in the mounting frame 7 on the pipe 10. The components in the inner mechanism are placed in relation to each other in the same way as described above in FIG. 2*a*. The wedges 1 are spanned out towards the mounting frame 7 as a result of a pressured force 13 from for instance a ROV (see also FIG. 1*b*).

In FIG. 3*a* it is illustrated how the sensor housing 6 and the inner mechanism preferably are surrounded by an outer cap 8, which together with the rear piece 9 comprises a compete sensor 6*b*. The outer cap 8 holds the inner mechanism comprising the sensor housing 6 in place, and protects it from the surroundings. The cap 8 has a "window" providing an opening for the protruded parts of the wedges 1 and are held in place themselves by a rear piece 9. The rear piece 9 constitutes an extension of the sensor housing 6. The cap 8 has protruding locking pins 11 adapted to go into locking tracks 12 in the mounting frame 7 during installation.

FIG. 3*b* illustrates the components of the locking mechanism when it is under influence by a force 13 from for instance a ROV pushing the complete sensor 6*b* into the mounting frame 7. The ROV grips a handle constituting an extension of the outer cap 8 and pushes the whole device in towards the pipe 10. The sensor housing 6 with mounted rear piece 9 is not locked to the outer cap 8. As a result of the pressured force 13, the spring 8 is compressed by contact between the sensor 6*a* and the pipe 10, and the wedges 1 slide up the inclined surface 3 and the conic ring 4. The protruded part of the wedges 1 will then be pushed out through the "windows" in the outer cap 8, and span out towards the mounting frame 7 so that the sensor housing 6 is centred in the mounting frame 7 with good and solid side support.

FIG. 4 shows a complete sensor 6*b* in the mounting frame 7 in locked position towards the pipe 10. By gradually increasing spring pressure during mounting, the locking pins 11 on the outer cap 8 will be guided into locking tracks 12 in the mounting frame 7. By unloading the outer force influence 13, the complete sensor 6*b* will now be locked with constant spring pressure towards the pipe 10. Sideways, it is now only the plastic wedges 1 spanning in towards the mounting frame 7. An alternative way of fastening the sensor 6*a* in the mounting frame 7 is shown in the Norwegian patent application 2006 1860.

The mounting frame 7 is in advance, fixedly mounted on the pipe 10, and is designed so that the complete sensor 6*b* will fit into and be secured with a robust locking and stable acoustic contact in towards the pipe 10.

Components as mounting frame 7, sensor housing 7, rear piece 9, outer cap 8, helical spring 2, flat disk 5 and conical ring 4 will preferably be of metal, normally stainless steel or titan, out from requirements to strength and robustness during the conditions and surrounding the equipment will operate. The wedges 1 will preferably be of a strong material with substantially lower acoustic impedance than metal, for instance a strong industrial plastic. However, the invention is not limited to these choices of materials. For instance, inclined surface 3, flat disk 5 and conic ring 4 could be non-metallic, given that strength and surface friction beyond that maintains the function of the mechanism. The wedges 1 can also be of a material or a combination of materials where the considerations regarding large acoustic impedance contrast towards the sensor housing 6 and the mounting frame 7 is not necessarily protected. Wedges 1 of for instance metal will fully maintain the principle and function for attaching sensor 6*a*, but the function of the wedges 1 as possible acoustic barrier will then be reduced and substantially limited to the effect of a small contact surface towards the mounting frame 7.

The locking device will be attachable to a pipe 10 with a diameter in the range of 100-300 mm, and the mounting frame 7 and the complete sensor 6*b* will for instance be approximately 700 mm long.

The mechanical components can be untreated, but they are, especially for metal parts, preferably surface treated for increased resistance towards corrosion and growing. For metallic parts where slide surfaces constitutes it further concerns that they are preferably coated with a material with low surface friction, for instance a Teflon based product. Cathodic protection of the metal parts is also possible.

A preferred embodiment of the present invention includes wedges 1 designed to together constitute a ring shape tightly surrounding the circumference of the sensor housing 6. Preferably, three wedges 1 are changed around the circumference.

The wedges 1 are not directly connected to each other or the sensor housing 6, but are held in place by an outer cap 8. The inclined surface 3 spanned out by the wedges 1 is also ring shaped, an inclined surface 3 on the sensor housing 6 itself and a conic ring 4, respectively. The basic principle for the invention is not dependent on this. Alternative embodiments can for instance comprise two or more wedges 1 and accompanying inclined surface 3 not necessarily constituting a ring shape. It is neither a requirement that the inclined surface 3 is designed as a part of the sensor housing 6; it is sufficient that the inclined surface 3 is in mechanical connection with this. The wedges 1 can further be held in place by other alternative solutions, for instance with a resilient or elastic connection mutually between the wedges 1, or with other forms of mechanical blocking out from the sensor housing 6. In this way, alternative embodiments of the invention can be realised without a surrounding outer cap 8.

In a preferred embodiment of the present invention, a flat disk 5 is placed behind the foremost wedge set 1 to secure a defined glide surface in the transition towards the helical spring 2, and an identical flat disk 5 is arranged behind the rear wedge set to secure identical friction conditions, so that the rear and foremost wedges 1 goes equally. The functionality of the invention is not dependent on that such insertions are designed as flat disks 5. Alternative embodiments can take several shapes given that the surface laying towards the wedges 1 is adapted to these, and maintains the function as gliding surface, and that the insertions apart from that is mechanical adapted to the adjacent parts. In principle, the rear insertion can possibly also be omitted completely.

A preferred embodiment of the present invention has at least one set of wedges 1 in front and at least one set of wedges 1 in the rear edge of the sensor housing 6, for secure sideways support. Alternative embodiments can comprise fewer sets of wedges 1 (i.e. one or more) and additional support in another shape, for instance by an elastic connection. The additional support can possibly be attended to by the locking mechanism for spring pressure itself.

The principle for locking the spring load is submitted to the present invention. For equipment mounted in relation to pipes on the sea floor, several known solutions and many variants of these are known, for instance "J-slot", spring loaded locking segments spanning outwards, and so-called "Collect-connector". The realisation here uses preferably a "J-slot" type of connection 12 (see FIG. 4), but alternative embodiments can also comprise other principles. This comprises also variants of screwed fastening and bayonet connection.

The invention claimed is:

1. Device for mounting in a fixed mounted frame (7) on a subsea pipe characterized by
   a locking device comprising a sensor housing (6),
   a spring (2) surrounding the sensor housing (6),
   at least one wedge (1) placed in one of the ends of the spring (2),
   and an edge (5a) placed in the other end of the spring (2),
   where the sensor housing (2) is arranged to be guided into the mounting frame (7),
   that a force (13) is applied in the longitudinal axis of the sensor housing (6) so that the spring (2) is compressed and the wedge(s) (1) are radial spanned out towards the mounting frame (7) to centre and support the sensor housing (6) in the mounting frame (6),
   the sensor housing (6) is designed to fit in the mounting frame (7),
   the at least one wedge (1) is arranged to function as acoustic barrier towards the mounting frame (7),
   and that the at least one wedge (1) is of a material with substantially less acoustic impedance than the metallic sensor housing (6).

2. Device according to claim 1, wherein the sensor housing (6) comprises a passive acoustic sensor (6a), arranged to be in contact with the pipe (10).

3. Device according to claim 1, wherein said at least one wedge (1) is designed to be able to slide up towards an inclined surface (3) machined on the sensor housing (6).

4. Device according to claim 1, wherein said at least one wedge (1) is designed to slide up towards an inclined surface on a conic ring (4) placed behind the spring (2).

5. Device according to claim 1, wherein an outer cap (8) surrounds the sensor housing (6), spring (2) and wedge(s) (1), and has holes giving opening for said at least one wedge (I).

6. Device according to claim 5, wherein a rear piece (9) being and extension of the sensor housing (6) holds the outer cap (8) in place.

7. Device according to claim 1, comprising at least two locking pins (11) on the outer cap (8) and goes into adapted locking tracks (12) in the mounting frame (7) for fixed mounting of the sensor housing (6) with constant spring pressure towards the pipe (10).

8. Device according to claim 1, wherein said at least one wedge (1) placed in the one end of the spring (2) is constituted by two or more wedge parts distributed around the circumference of the sensor housing (6).

9. Device according to claim 1, wherein a first flat disk (5) is arranged between said at least one wedge (1) and the spring (2).

10. Device according to claim 1, wherein at least one second wedge (1) is placed in the second end of the spring (2) in relation to said at least one wedge (1).

11. Device according to claim 10, wherein a second flat disk (5) is arranged between said at least one second wedge (1) and the edge (5a).

* * * * *